United States Patent

Alms et al.

Patent Number: 5,481,033
Date of Patent: Jan. 2, 1996

[54] PURIFICATION PROCESS FOR AROMATIC DICARBOXYLIC ACIDS

[75] Inventors: Gregory R. Alms, Hockessin; Michael R. Samuels, Wilmington, both of Del.

[73] Assignee: E. I. Du Pont de Nemours and Company, Wilmington, Del.

[21] Appl. No.: 362,334

[22] Filed: Dec. 22, 1994

[51] Int. Cl.$^6$ .................................................... C07C 51/42
[52] U.S. Cl. ............................................. 562/486; 562/485
[58] Field of Search ........................... 560/78; 562/485, 562/486

[56] References Cited

U.S. PATENT DOCUMENTS

| | | | |
|---|---|---|---|
| 4,317,923 | 3/1982 | Imai | 562/487 |
| 5,097,066 | 3/1992 | Holzhauer et al. | 562/487 |
| 5,149,867 | 9/1992 | Chen et al. | 562/486 |

FOREIGN PATENT DOCUMENTS 49-123306  10/1974  Japan.

Primary Examiner—José G. Dees
Assistant Examiner—Samuel Barts

[57] ABSTRACT

Disclosed is a process for the purification of aromatic dicarboxylic acids in which the salt of an aliphatic diamine and an aromatic dicarboxylic acid is formed in an aqueous solvent, recrystallized, and contacted with an aliphatic dicarboxylic acid in an aqueous solvent such that the aromatic dicarboxylic acid is recoverable in the form of a purified precipitate. The remaining aqueous solute is a salt of the aliphatic diamine and aliphatic dicarboxylic acid and can be used as a starting material in the manufacture of certain polyamides (nylons). The invention is particularly applicable for purifying 2,6-naphthalene dicarboxylic acid, which is difficult otherwise to purify.

12 Claims, No Drawings

PURIFICATION PROCESS FOR AROMATIC DICARBOXYLIC ACIDS

FIELD OF THE INVENTION

This invention relates to a process for the purification of aromatic dicarboxylic acids.

BACKGROUND OF THE INVENTION

Aromatic dicarboxylic acids are important items of commerce. While they have varied uses as chemical intermediates, probably their largest use are as monomers for use in polymerizations, particularly to make thermoplastic polyesters and polyamides. For this and other purposes, very pure materials are, generally, required and new methods of purifying such aromatic dicarboxylic acids are constantly being sought.

Aromatic dicarboxylic acids such as phthalic acid, isophthalic acid and terephthalic acid may be prepared by an oxidation process in which mixed alkyl aromatics or particular xylenes are subjected to an oxidation reaction with heavy metal salts and bromine acting as catalysts. For example, paraxylene may be oxidized to terephthalic acid in the liquid phase with a catalyst consisting of cobalt acetate and hydrogen bromide dissolved in acetic acid. An oxygen containing gas such as air is injected into the reactor which is maintained at an elevated temperature of around 200° C. and superatmospheric pressures of about 10 atmospheres. The amount of air which is injected into the reactor is sufficient to maintain an excess of oxygen in the off-gas over the stoichiometric requirement. The liquid which is drawn from the reactor will contain about 25 to about 35 percent solids. These solids can contain the desired terephthalic acid as well as contaminants or impurities in the form of the monocarboxylic acid, aldehydes, unoxidized materials, over oxidized materials, catalyst residues, etc. Most or all of these contaminants or impurities may affect the usefulness of the aromatic dicarboxylic acid as a monomer for polymerizing polyesters and polyamides.

Japanese Patent Application 51-52163 describes a process for the purification of 2,6-naphthalene dicarboxylic acid by formation and purification of its ammonium salt. There is no mention of using aliphatic diamines or recovery of useful byproduct salts in the process.

It is an object of the present invention to provide a convenient, efficient and effective process for making purified aromatic dicarboxylic acid from relatively impure aromatic dicarboxylic acid. The process described herein results in byproducts which are useful in the manufacture of nylons.

SUMMARY OF THE INVENTION

This invention relates to a process for the purification of aromatic dicarboxylic acids in which the salt of an aliphatic diamine and an aromatic dicarboxylic acid is formed in an aqueous solvent, crystallized, and contacted with an aliphatic dicarboxylic acid in an aqueous solvent such that the aromatic dicarboxylic acid is recoverable in the form of a purified precipitate. The remaining aqueous solute is a salt of the aliphatic diamine and aliphatic dicarboxylic acid and can be used as a starting material in the manufacture of certain polyamides (nylons). The invention is particularly applicable for purifying 2,6-naphthalene dicarboxylic acid, which is difficult otherwise to purify. Specifically, the present invention relates to a process for the purification of an aromatic dicarboxylic acid, said process comprising the steps of:

(A) contacting an aromatic dicarboxylic acid with an aliphatic diamine in the presence of water to form an aqueous salt solution containing a salt formed by the aromatic dicarboxylic acid and the aliphatic diamine, wherein the aliphatic diamine is of the formula $H_2NR^1NH_2$

and $R^1$ is a saturated hydrocarbylene containing 4 to 14 carbon atoms;

(B) recovering from the aqueous salt solution the salt formed by the aromatic dicarboxylic acid and the aliphatic diamine;

(C) dissolving said recovered salt in an aqueous solvent to form a second aqueous salt solution containing the salt formed by the aromatic dicarboxylic acid and the aliphatic diamine;

(D) contacting said second aqueous salt solution with an aliphatic dicarboxylic acid of the formula $HO_2CR^2CO_2H$

where $R^2$ is a saturated hydrocarbylene containing 2 to 12 carbon atoms; and (E) recovering a precipitated purified aromatic dicarboxylic acid.

DETAILED DESCRIPTION

The process described herein is one for the purification of an aromatic dicarboxylic acid. By an "aromatic dicarboxylic acid" is meant a dicarboxylic acid in which the two carboxyl groups are each directly bound to a carbon atom of an aromatic ring. The aromatic dicarboxylic acid may contain one or more aromatic rings (which may be fused or unfused), and the two carboxyl groups may be bound to one or two different aromatic rings. The aromatic dicarboxylic acids may contain other groups or substituents which do not interfere with this purification process, such as alkyl or alkylene. The present process is useful for purifying many aromatic dicarboxylic acids including, but not limited to, benzene dicarboxylic, naphthalene dicarboxylic, and bibenzoic acids. The present process is particularly useful for purifying aromatic dicarboxylic acids such as isophthalic acid, terephthalic acid, naphthalene dicarboxylic acid, and bibenzoic acid. The present process is most preferably used to purify 2,6-naphthalene dicarboxylic acid and 4,4'-bibenzoic acid.

By an "aqueous solvent" is meant a solvent which contains more than 50% by weight of water, preferably more than 85% by weight of water, and most preferably, is 100% water. If a cosolvent is used with the water, it must be miscible with water in the proportion it is used. Suitable cosolvents include lower alcohols such as methanol and ethanol, and lower ketones such as acetone.

Aliphatic diamines useful in the present process include diamines of the formula $H_2NR^1NH_2$, where $R^1$ is a "saturated hydrocarbylene", meaning a divalent radical containing only carbon and hydrogen, and which contains no unsaturation such as olefinic, acetylenic or aromatic groups. It is contemplated that saturated hydrocarbylene can include cycloaliphatic rings. Useful groups $R^1$ groups include— $(CH_2)_n$— wherein n is 4 to 14, —CH$_2$CH(CH$_3$)CH$_2$CH$_2$CH$_2$—, and

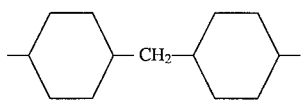

It is preferred if R$^1$ is —(CH$_2$)$_n$— wherein n is 4, 6, 8, 10 or 12, and it is more preferred if n is 6.

The aliphatic dicarboxylic acid used in the present process is of the formula HO$_2$CR$^2$CO$_2$H. Useful R$^2$ groups include —(CH$_2$)$_m$— wherein m is 2 to 12. It is preferred if m is 4 or 10, and it is especially preferred if m is 4.

An aqueous solution of the salt of the (crude) aromatic dicarboxylic acid and the aliphatic diamine can be prepared by addition of the aromatic dicarboxylic acid and the aliphatic diamine to an aqueous solvent (preferably contacting the aromatic dicarboxylic acid and the aliphatic diamine in the presence of water). Heating near or to the boiling point of the solution (pressure may be used to increase the boiling point, but is usually not needed), speeds up formation of the salt and will usually result in more of the salt being dissolved than at lower temperatures. Although not critical, it is preferred to use a molar ratio of aromatic dicarboxylic acid to aliphatic diamine which is approximately 1:1. This results in the most efficient use of the materials. The solubility of the salt of the aromatic dicarboxylic acid and aliphatic diamine in the aqueous solvent will vary, depending on the particular aromatic dicarboxylic acid and aliphatic diamine used. Generally speaking, the salt will be more soluble when fewer carbon atoms are present in the aromatic dicarboxylic acid and/or aliphatic diamine. It is often preferred to use as little aqueous solvent as necessary. Such an approach will often result in a higher yield upon crystallization of the salt.

If upon formation and dissolution of the salt some insolubles remain, these can be removed by any common means such as filtration. If the solution of the salt between the aromatic dicarboxylic acid and aliphatic diamine is highly colored, or contains impurities, such as metals, that are readily adsorbed, the solution may optionally be treated with an adsorbent such as activated carbon. The adsorbent and adsorbed impurities can be removed easily by suitable means such as filtration or decantation.

The salt of the aromatic dicarboxylic acid and aliphatic diamine is then allowed to precipitate (crystallize), most typically by cooling the solution, so as to reduce the solubility of the salt. After precipitation, the solid salt is separated from the aqueous solvent by any appropriate means, such as filtration, decantation or centrifugation. If appropriate, the solid salt may be washed with a small amount of liquid to remove adhering aqueous solvent. If sufficiently pure at this point the salt may be used directly to prepare the pure aromatic dicarboxylic acid. However, if needed, one or more recrystallizations (and contact with an adsorbent, if appropriate) may be done until the salt of the aromatic dicarboxylic acid and aliphatic diamine is pure enough to yield an aromatic dicarboxylic acid of the desired purity.

Recrystallization may be carried out by dissolving the salt of the aromatic dicarboxylic acid and aliphatic diamine in a minimum amount of aqueous solvent at elevated temperature, and then allowing the salt to crystallize (precipitate) by lowering the temperature. The solid salt is separated from the aqueous solvent by a suitable means such as filtration, and optionally washing with water. Other techniques for purifying the salt such as, zone refining may be used.

Once a salt of the aromatic dicarboxylic acid and aliphatic diamine of suitable purity (so that aromatic dicarboxylic acid of suitable purity will be obtained) is obtained, such salt is dissolved in an aqueous solvent and an aliphatic dicarboxylic acid is added. This is preferably done at elevated temperature, up to the boiling point of the solution, so as to render the "by product", the salt of the aliphatic diamine and aliphatic dicarboxylic acid, soluble. Upon addition of the aliphatic dicarboxylic acid, which is preferably somewhat soluble in water, the aromatic dicarboxylic acid, which usually has very low solubility in the aqueous solvent, at all temperatures, precipitates and may be removed by filtration, decantation, centrifugation or other suitable means. The solid aromatic dicarboxylic acid may then be extracted and/or washed with solvent and dried before use, if desired.

In order to most efficiently use the materials, the molar ratio of salt to aliphatic dicarboxylic acid used should be about 1:1. After the solid aromatic dicarboxylic acid is removed, the remaining aqueous solvent contains a salt of the aliphatic diamine and aliphatic dicarboxylic acid. It is well known that the aqueous solutions of such salts may be used to prepare aliphatic polyamides (also known as nylons) by simply heating, see for instance Ullmann's Encyclopedia of Industrial Chemistry, 5th Ed., B. Elvers., et al., Editors, Vol. A21, VCH Verlaggesellschaft mbH, D6940, Weinheim, 1992, p. 179–192, and references therein, the disclosure of which is hereby incorporated by reference. Thus, "neutralization" of the salt of the aromatic dicarboxylic acid and aliphatic diamine to recover the pure aromatic dicarboxylic acid does not result in production of an unwanted byproduct, but rather produces a salt which itself may be used to produce a useful product. This reduces waste, potential environmental contamination, and cost.

EXAMPLES

Example 1

Distilled water (800 ml) was placed in a 2 liter round bottom flask with magnetic stirrer, heating mantle, and reflux condenser. The water was heated to 100° C. (boiling), and 112.0 g of hexamethylene diamine (HMD) and 200 g of crude 2,6-naphthalene dicarboxylic acid (2,6N) from Amoco Chemical Co. were added slowly. As the 2,6N was added it dissolved very quickly, forming a deep red solution. Five (5) heaping teaspoons of fresh 10 mesh Darco® activated charcoal were added with stirring. The solution was hot filtered using a heated vacuum (but without using vacuum) filter with a double layer of filter paper to trap the carbon particles and any precipitated catalyst residues. The tiltrate was cooled in an ice/water mixture to about 5° C. A crop of light brown crystals (HMD-2,6N salt) precipitated from the solution. The crystals were separated from the liquor by cold filtration through a porous glass filter funnel. The recovered crystals were washed 2 times with a total of approximately 50 ml of cold distilled water.

Distilled water (750 ml) was added to a 2 liter heated round bottom flask, and heated to boiling. The washed salt crystals were dissolved in the boiling water. Five more teaspoons of fresh Darco® activated carbon were added and the boiling slurry stirred for about 15 minutes. The mixture was hot filtered through a heated filter, and the tiltrate cooled to about 5° C. to precipitate the salt a second time. The filtrate solution was a light straw color.

The recovered solids were washed twice with a total volume of 50 ml of cold distilled water. The recovered crystals were redissolved in 1500 ml of boiling distilled water in a 5 liter round bottom flask. The solution was a pale straw yellow.

Adipic acid (135 g) was added to the hot salt solution. As the adipic acid dissolved, a frothy white precipitate of 2,6N formed, in some cases appearing to encase the crystals of dissolving adipic acid. The mixture was boiled for 10 minutes and then filtered hot. The 2,6N cake was washed once with cold water on the filter, and the cake transferred to a 2000 ml round bottom flask. One liter of distilled water was added to the recovered 2,6N, .and the slurry boiled for 30 minutes. The tiltrate solution contained the HMD-adipic acid salt formed during the 2,6N recovery step, and was a pale yellow color. On cooling, off-white excess adipic acid precipitated from the solution.

Heat was then removed from the 2,6N/water slurry and the slurry allowed to cool to room temperature over night. The extracted 2,6N was recovered by room temperature filtration followed by washing and drying in a vacuum oven. Over 140 g of purified 2,6N were recovered. The material had a snow white color, and a Differential Scanning Calorimetry melting point of 456.4° C. as compared to 448° C. for the original crude and 459° C. for a highly purified sample of 2,6N (DSC heating rate of 25° C./min). The highly purified 2,6N sample was prepared by hydrolysis of distilled dimethyl ester (of 2,6N) supplied by Amoco Chemicals. It is believed that hydrolysis of the the ester was greater than 99% completed.

What is claimed is:

1. A process for the purification of an aromatic dicarboxylic acid, said process comprising the steps of:
   (A) contacting an aromatic dicarboxylic acid with an aliphatic diamine in the presence of water to form an aqueous salt solution containing a salt formed by the aromatic dicarboxylic acid and the aliphatic diamine, wherein the aliphatic diamine is of the formula $H_2NR^1NH_2$ and R is a saturated hydrocarbylene containing 4 to 14 carbon atoms;
   (B) recovering from the aqueous salt solution the salt formed by the aromatic dicarboxylic acid and the aliphatic diamine;
   (C) dissolving said recovered salt in an aqueous solvent to form a second aqueous salt solution containing the salt formed by the aromatic dicarboxylic acid and the aliphatic diamine;
   (D) contacting said second aqueous salt solution with an aliphatic dicarboxylic acid of the formula $HO_2CR^2CO_2H$ where $R^2$ is a saturated hydrocarbylene containing 2 to 12 carbon atoms; and
   (E) recovering a precipitated purified aromatic dicarboxylic acid.

2. A process as recited in claim 1 wherein said aromatic dicarboxylic acid is selected from the group consisting of benzene dicarboxylic acid, naphthalene dicarboxylic acid, and bibenzoic acid.

3. A process as recited in claim 2 wherein said aromatic dicarboxylic acid is selected from the group consisting of 2,6-naphthalene dicarboxylic acid and 4,4'-bibenzoic acid.

4. A process as recited in claim 1 wherein $R^1$ is selected from the group consisting of $-(CH_2)_n-$ where n is 4 to 14,
$-CH_2CH(CH_3)CH_2CH_2CH_2-$, and

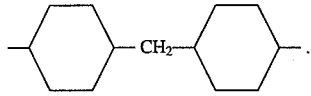

5. A process as recited in claim 4 wherein $R^1$ is $-(CH_2)_n-$ and n is 4, 6, 8 10 or 12.

6. A process as recited in claim 5 wherein n is 6.

7. A process as recited in claim 1 wherein $R^2$ is $-(CH_2)_m-$ and m is 2 to 12.

8. A process as recited in claim 7 wherein m is 4 or 10.

9. A process as recited in claim 1 further comprising the step of using activated carbon as an adsorbent.

10. A process as recited in claim 1 wherein said aqueous solvent is 100% water.

11. A process as recited in claim 1 wherein $R^1$ is $-(CH_2)_n-$ and n is 6, $R^2$ is $-(CH_2)_m-$ and m is 4, and said aqueous solvent is 100% water.

12. A process as recited in claim 1 wherein said aromatic dicarboxylic acid is selected from the group consisting of isophthalic acid, terephthalic acid, naphthalene dicarboxylic acid, and bibenzoic acid.

* * * * *

UNITED STATES PATENT AND TRADEMARK OFFICE
CERTIFICATE OF CORRECTION

PATENT NO. : 5,481,033

DATED : Jan. 2, 1996

INVENTOR(S) : Alms et al.

It is certified that error appears in the above-identified patent and that said Letters Patent is hereby corrected as shown below:

Claim 1, column 5, line 37, delete "Ris" and insert -$R^1$ is-

Signed and Sealed this

Twenty-first Day of May, 1996

*Attest:*

BRUCE LEHMAN

*Attesting Officer*     *Commissioner of Patents and Trademarks*